United States Patent [19]

Covic et al.

[11] Patent Number: 4,466,112
[45] Date of Patent: Aug. 14, 1984

[54] VARIABLE DETECTOR APERTURE

[75] Inventors: John Covic, Wickliffe; Roland W. Carlson, Lyndhurst, both of Ohio

[73] Assignee: Technicare Corporation, Cleveland, Ohio

[21] Appl. No.: 344,244

[22] Filed: Jan. 29, 1982

[51] Int. Cl.³ .............................................. G03B 41/16
[52] U.S. Cl. ........................................ 378/7; 378/150
[58] Field of Search .......................... 378/7, 150, 160

[56] References Cited

U.S. PATENT DOCUMENTS

| | | | |
|---|---|---|---|
| 2,851,610 | 9/1958 | Akashi | 378/150 |
| 2,993,993 | 7/1961 | Delong | 378/150 |
| 3,238,371 | 3/1966 | Furnas, Jr. | 250/105 |
| 3,275,831 | 9/1966 | Martin | 378/160 |
| 4,071,771 | 1/1978 | Covic et al. | 250/511 |
| 4,143,273 | 3/1979 | Richey et al. | 250/445 T |
| 4,190,773 | 2/1980 | Braden et al. | 250/445 T |
| 4,277,684 | 7/1981 | Carson | 378/7 |
| 4,277,685 | 7/1981 | Covic et al. | 250/445 T |

Primary Examiner—Craig E. Church
Attorney, Agent, or Firm—Michael A. Kaufman

[57] ABSTRACT

In a rotating fan beam tomographic scanner there is included a variable detector aperture housed within a radiation scatter shield. The scanner includes a diverging source of penetrating radiation which is directed toward a patient receiving section for passing a fan shaped beam of radiation through a planar section of the patient. The incident radition beam is attenuated during its passage through the patient receiving section and the transmitted beam passes from the patient receiving section until it impinges on a plurality of detectors for eventual reconstruction into a visible image. The variable detector aperture controls the thickness of the fan shaped beam and hence limits the amount of radiation impinging on the detectors. The aperture includes a pair of elongated beam thickness defining members having an opening therebetween and rotatable relative to the scanning plane. The opening between the two members in a direction transverse to the scanning plane defines the thickness of the attenuated fan beam passing therethrough.

7 Claims, 18 Drawing Figures

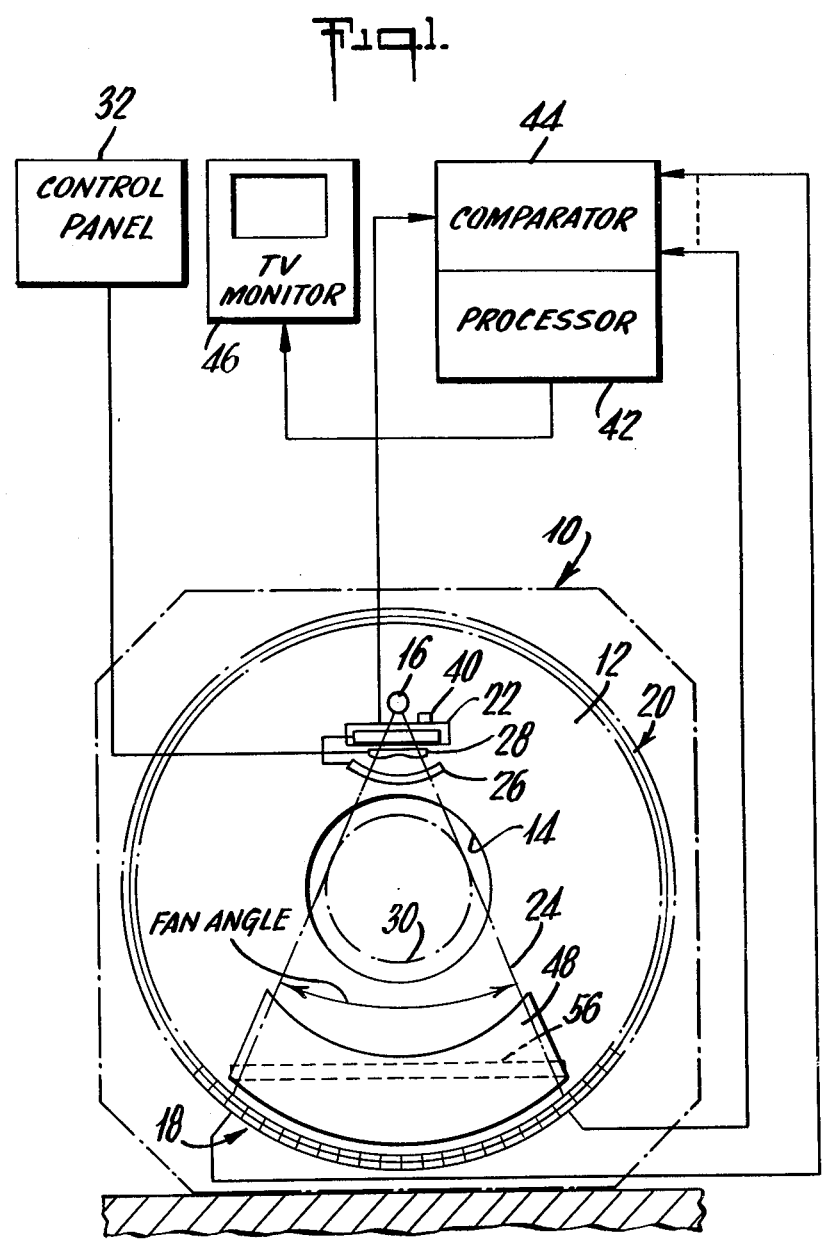

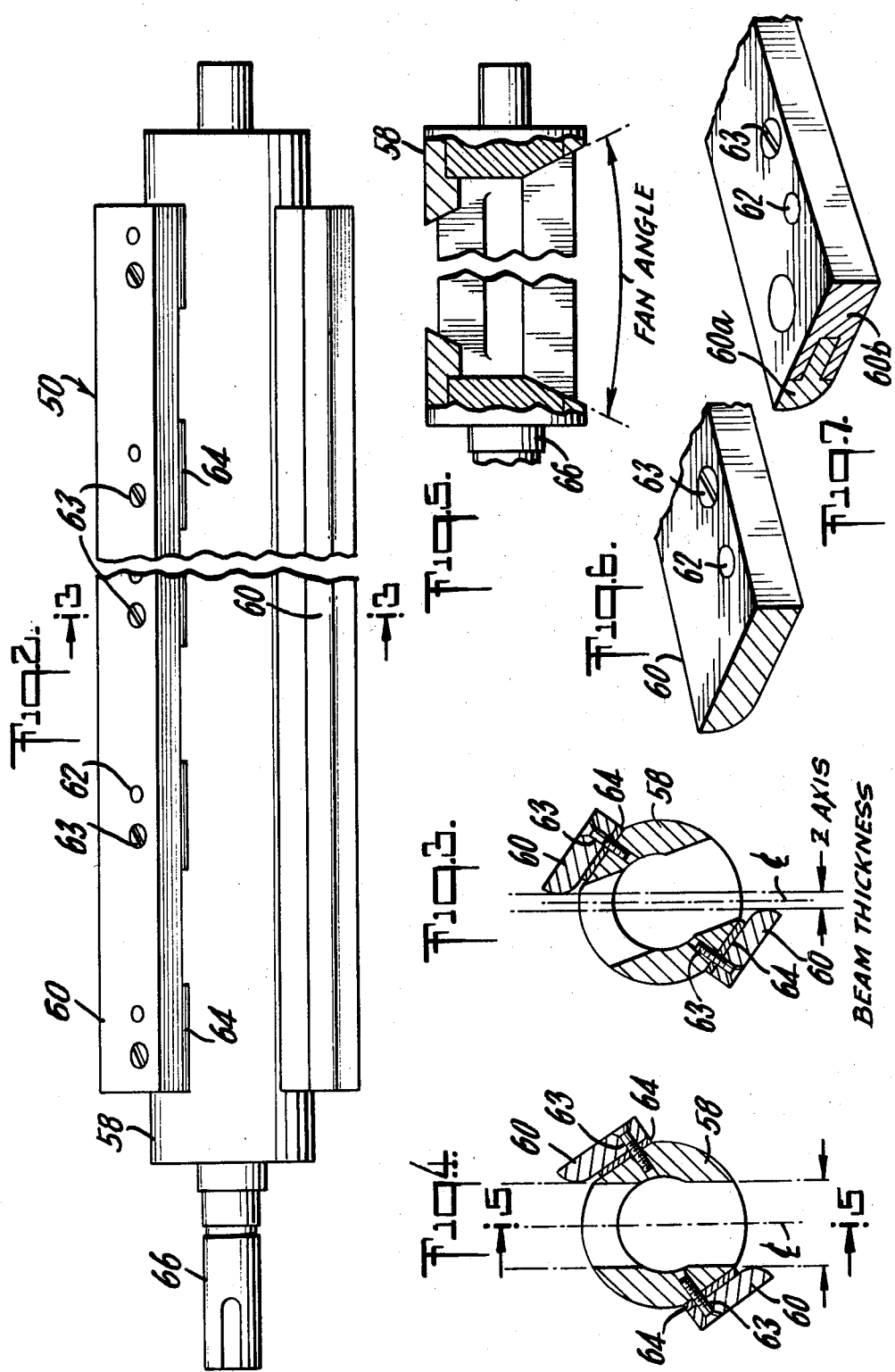

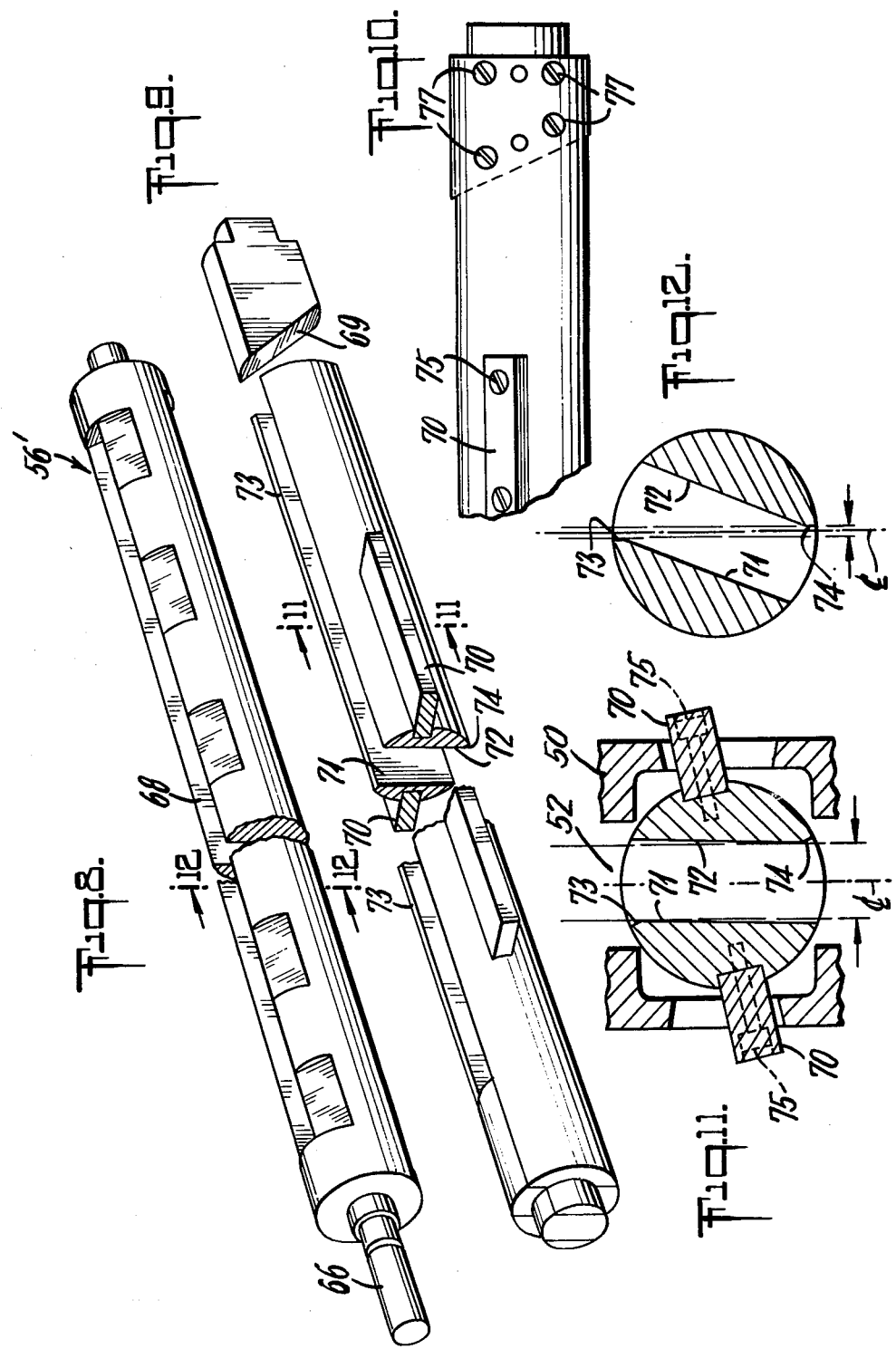

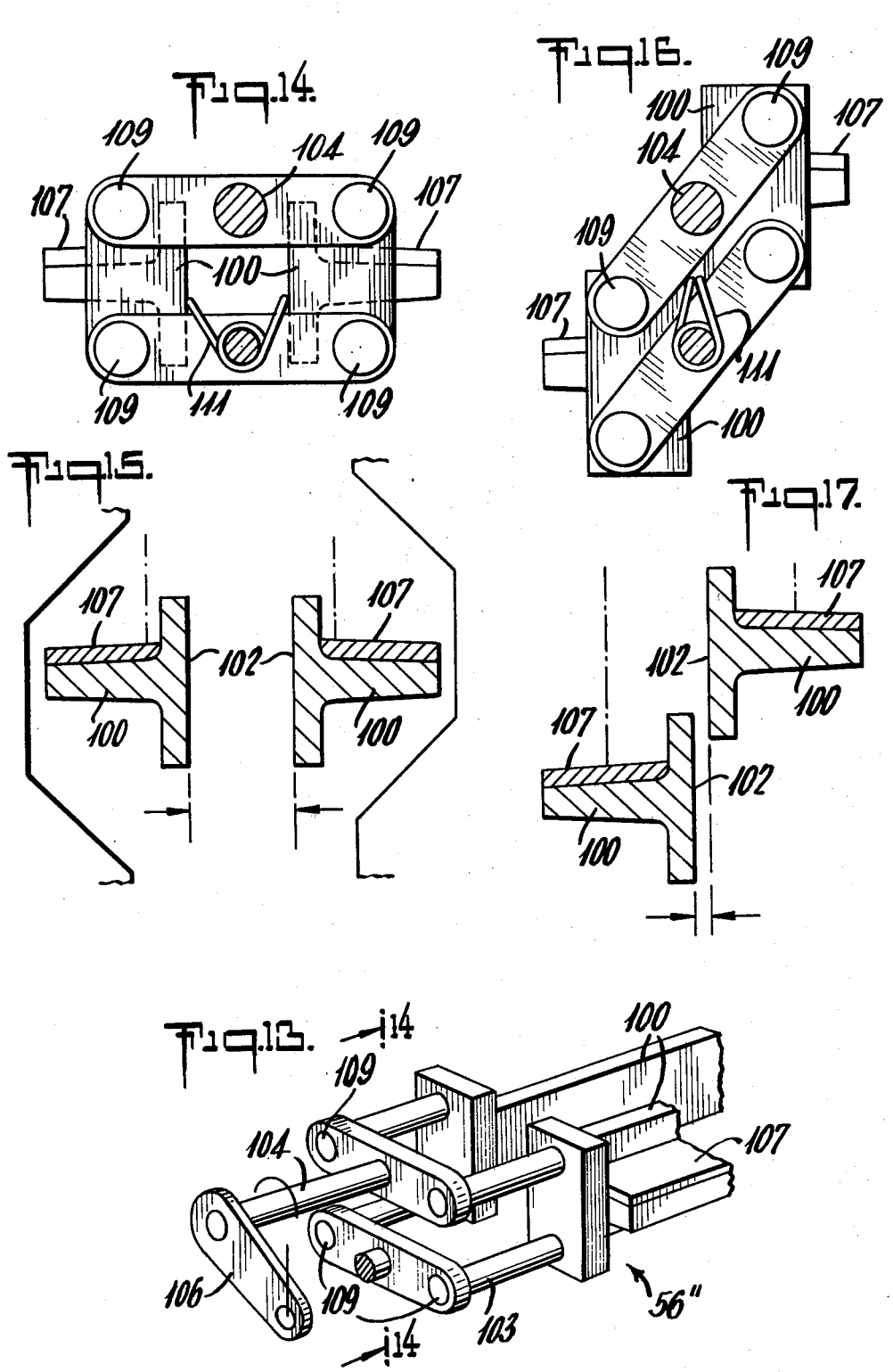

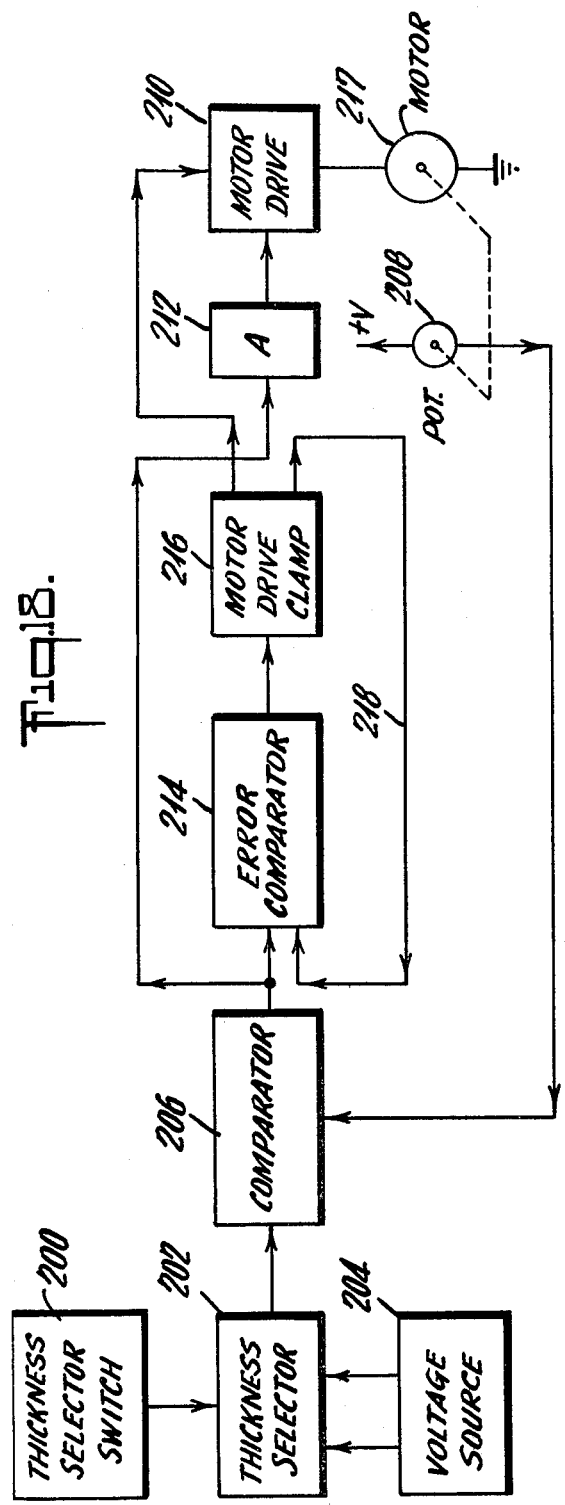

VARIABLE DETECTOR APERTURE

TECHNICAL FIELD

This invention relates generally to radiographic apparatus primarily for use in computerized axial tomography and more particularly to a receiver collimator structure therefor. Specifically, the invention is concerned with an apparatus which automatically controls the thickness of X-ray beams in X-ray diagnostic equipment as particularly adapted for controlling the amount of attenuated radiation that is detected.

BACKGROUND ART

Rotating fan beam tomographic scanners normally comprise a circular area in which a patient or object to be examined is placed. A source of penetrating radiation such as X or gamma radiation is mounted to move in an arc adjacent the patient circle in order to rotate a beam of radiation at least partially around the patient. An arc of radiation detectors for measuring the intensity of radiation passing through the patient are positioned opposite the patient circle from the source of radiation. In some scanner models, an arc of radiation detectors rotates with the radiation source, while in others the detectors are stationary. A processing means transforms the intensity measurements of the arc of detectors into a visual display of the planar section of the patient being scanned.

Excessive radiation can cause two types of image degradation which is discussed in applicants' earlier filed application, now U.S. Pat. No. 4,277,685, the disclosure of which is incorporated herein by reference. As was taught in said earlier patent, scattered radiation travels in an unknown path through objects of unknown attenuation and creates erroneous data signals and noise. Hence, scatter can reduce the resolution of the image produced on the visual display. The '685 patent teaches means for shaping the cross-sectional dimensions of the radiation beam, specifically the incident beam, i.e., the beam emitted by the X-ray source before it is attenuated by the object being scanned. The '685 patent also noted that a detector (alternately referred to as receiver) collimator may additionally be used. The detector collimator serves the purpose primarily of eliminating scattered radiation from the attenuated transmitted beam and is the primary object of the present invention. In addition to eliminating scattered radiation caused by the object being scanned, the inlet opening in the detector collimator must correspond to the opening provided by the source collimator so that all the radiation to which the patient is subjected and which contains information usable in producing a representative image is utilized.

Image reconstruction algorithms normally assume a constant slice thickness. Thus, variations in the thickness of the beam will cause degradation and inaccuracies in the reconstructed image. It is therefore essential that the beam thickness be uniform throughout the fan. Previously, the slice thickness of the transmitted beam was determined by a pair of typically lead tipped aperture rings positioned immediately in front of the detectors and moved simultaneously together or apart relative to the center line of the X-ray beam in the Z axis. This conventional technique suffers from an accuracy problem since the large size of the rings causes them to flex and distort. Due to this distortion, the aperture opening can not be maintained accurate or uniform relative to the center line of the X-ray beam. The variations in the spacing between the two rings is particularly significant as the two rings are brought very close together. Thus, thin slices can not be made because of the dimensional deviations. In addition, the aperture opening varies with wear and tear of the rings.

SUMMARY OF THE INVENTION

We have discovered a variable detector aperture which accurately determines the slice thickness of the X-ray beam and which is generally uniform throughout the fan angle. A fan shaped penetrating X-ray beam is directed to a scan circle where it is attenuated by a planar section of a subject being scanned. The attenuated fan beam is transmitted from the scan circle to an arc of radiation detectors. Between the scan circle and the detectors receiving the attenuated radiation beam there is a scatter shield which blocks much of the scattered radiation. Disposed within the scatter shield is a pair of beam thickness defining members which are rotatable relative to the center line of the X-ray beam in the Z direction. One of said beam thickness defining members limits the thickness of the X-ray beam in the positive Z direction relative to the center line, while its cooperating counterpart limits the thickness of the X-ray beam in the negative Z direction. According to this convention, the width of the beam is in a direction parallel to the scan circle and the Z direction is orthogonal to the plane of the scan circle. Thus, the variation in the orthogonal spacing between the two thickness defining members determine the thickness of the transmitted beam.

BRIEF DESCRIPTION OF THE DRAWINGS

FIG. 1 is an overall system view of the computerized tomographic scanning system in combination with a detector collimator in accordance with the present invention;

FIG. 2 is a plan view of a preferred embodiment of the rotating detector aperture assembly according to the invention;

FIG. 3 is a section taken along lines 3—3 of FIG. 2 showing the aperture defining a relatively thin beam thickness;

FIG. 4 is a view similar to FIG. 3 showing the aperture of FIG. 2 in its openmost position;

FIG. 5 is a cross-sectional view taken along lines 5—5 of FIG. 4 showing the collimated angle of the scatter shield defining the beam width;

FIG. 6 is a detail of a portion of one of the beam thickness defining members of the preferred embodiment;

FIG. 7 is a view similar to FIG. 6 showing an alternate construction of one of the beam thickness defining members of the preferred embodiment;

FIG. 8 is a plan view similar to FIG. 2 showing an alternate embodiment of the rotating detector aperture assembly according to the present invention;

FIG. 9 shows a detector aperture assembly similar to FIG. 8 with lateral stiffeners to ensure uniform spacing throughout the width of the fan beam;

FIG. 10 is a detail of a portion of one end of the detector aperture of the alternative embodiment of FIG. 9;

FIG. 11 is a section taken along lines 11—11 of FIG. 9 illustrating the aperture in its openmost rotational orientation;

FIG. 12 is a section taken along lines 12—12 of FIG. 8 showing the aperture defining a relatively thin beam slice;

FIG. 13 is a perspective schematic of another alternate embodiment illustrating a parallel aperture assembly according to the invention which utilizes a pair of elongated generally T-shaped members;

FIG. 14 is a section taken along lines 14—14 of FIG. 13 showing the detector aperture in its openmost position;

FIG. 15 is a diagrammatical representation showing the generally T-shaped members in the orientation depicted in FIG. 14;

FIG. 16 is a section similar to FIG. 14 with the T-shaped members rotated to define a relatively thin beam;

FIG. 17 is a diagrammatic illustration corresponding to FIG. 16 showing the generally T-shaped members in the orientation depicted in FIG. 16; and FIG. 18 is a block diagram illustrating the control circuitry of the exemplary embodiments.

BEST MODE FOR CARRYING OUT THE INVENTION

Referring now to the drawings, FIG. 1 shows the general arrangement of a rotating fan beam type radiographic scanner incorporating the present invention. Such a scanner includes a stationary gantry 10 on which is mounted a rotatable member 12. In the center of the rotatable member is an opening 14 for receiving a patient or object to be scanned. On the rotatable member 12 is a source of radiation 16 mounted for rotation concentrically about the center of the patient opening.

An arc of radiation detectors 18 is disposed along the periphery 20 between the gantry 10 and the rotatable member 12. The radiation detectors 18 are positioned to receive radiation passing through the patient receiving opening. The arc of radiation detectors may be a relatively short arc mounted on the rotatable member 12 such that the detectors rotate with the radiation source remaining across the patient from the source. Alternatively, a relatively long arc of detectors or an entire circle of detectors may be mounted on the gantry circumscribing much or all, respectively, of the periphery 20 such that, as the source rotates, stationary detectors remain positioned across the patient from the source. A source collimator assembly 22 is mounted on the rotatable member 12 contiguous with the radiation source 16. The collimator assembly variably defines the width of the beam of radiation. The beam dimensions can be described in terms of the beam thickness in the Z axis and in terms of fan angle 24 in the X-Y plane or in terms of the scan circle 30 diameter. That is, different fan angles span different widths or scan circles at the patient position.

The source fan angle and thickness may be continuously or incrementally adjustable as described in greater detail in U.S. Pat. No. 4,277,685. The thickness of the planar slice emitted by the source of radiation is controlled by a curved source aperture 26. The source side also includes a shaped radiation filter 28 described in U.S. Pat. No. 4,288,695.

Also illustrated in FIG. 1, is a scatter shield 48 which collimates the transmitted radiation beam before it impinges on the arc of detectors 18. Scatter shield 48 defines the width of the transmitted fan angle as shown in FIG. 5. The scatter shield also serves as the first barrier toward radiation scatter in the Z direction as shown in FIG. 11 by blocking the transmission of radiation impinging on its frontal portion 50 facing the scan circle. Between either sides of this frontal portion 50 is an inlet opening 52. Within scatter shield 48 is a rotatable detector aperture assembly 56 which further limits the thickness of the transmitted radiation beam, and which is described in greater detail in the several embodiments discussed hereinbelow.

The selection of the fan angle or scan circle diameter, the beam thickness on the source side as well as the beam thickness on the detector side, may be remotely selected from a control panel 32.

Also illustrated in FIG. 1, is a source radiation intensity measuring means or reference detector 40 for measuring the intensity of radiation before it reaches the patient. Tomographic scanners customarily derive their data from the amount of radiation absorbed by the body, i.e. the decrease in intensity of the beams of radiation due to attenuation as the beams pass through the patient. Measuring means 40 measures the radiation intensity before entering the scan circle in which a patient is normally located. The arc of detectors 18 measures the intensity after the radiation beams pass through the patient i.e., the intensity of the transmitted beam. The fan beam of radiation being divergent, adjustment must be made for the difference in cross-sectional area of the beam at the monitoring means 40 compared to the cross-sectional area at the detector arc 18. Data from both of these detectors is channelled to a processor 42 which may be designed in accord with signal processing circuitry such as referred to in U.S. Pat. No. 4,277,685 referred to hereinabove. Included in the processor 42 is a comparator 44 for adjusting the data from the arc of radiation detectors 18 by the pre-patient intensity measured by means 40.

The processor 42 transforms the attenuation data which it receives into a representation of the slice of the patient through which the fan shaped beam of radiation has passed. This representation may be in the form of a visual display on a television monitor 46.

FIG. 2 shows the preferred embodiment of a rotating aperture bar assembly referred to generally as 56. The bar assembly 56 includes a generally cylindrical slotted steel carrier 58 and a pair of diametrically opposed masks 60 which serve as radiation beam thickness defining members. Each of the masks 60 are mounted on the steel carrier by means of a plurality of dowel pins 62 and screws 63 attached through steel spacers 64. The rotating aperture bar assembly 56 is rotatable by a motor 217 shown schematically in the block diagram of FIG. 18 through drive shaft 66 which connects to the aperture bar assembly through a bearing journal 68. The masks 60 may be solid molybdenum bars as shown in FIG. 6 or, if some economy is sought, may be a lead-steel composition as shown in FIG. 7 with the tip 60a made of lead and the remaining body portion 60b made of steel, the crucial consideration being that at least the tip portion be made of a heavy dense material to effectively stop the passage of X-rays.

FIG. 5 illustrates the fan angle or beam width of the transmitted beam, i.e. the beam that has passed through the scan circle on its passage toward the arc of detectors. FIGS. 3 and 4 illustrate a cross-section of the fan beam, showing the beam thickness in the Z axis or the orthogonal direction, perpendicular to the scan circle. The extent of the beam thickness is controlled by the orthogonal opening between the tips of the two masks 60. The two masks 60 are stationary relative to each other since they are both secured to the rotating aperture bar assembly. Thus, the absolute spacing between them remains constant during rotation; however, the spacing between them in the Z axis varies as they are rotated relative to the center line of the beam thickness. Thus, as illustrated in FIG. 4, as the assembly 56 is rotated so that the tips of the masks are generally away from the North and South positions, the beam thickness tends to be relatively large, whereas when the assembly 56 is rotated counterclockwise relative to that position, as shown in FIG. 3, the beam thickness gradually narrows. As indicated by these illustrative figures, the beam thickness can be varied through a continuous spectrum from fully closed to fully open which in the preferred embodiment corresponds to 10 millimeters. Alternatively, the motor and drive assemblies can be designed to provide discrete slice thickness selections such as 10, 7, 5, and even 2 millimeter thickness. Thickness selection may be conveniently selected by the operator at the control panel 32.

FIGS. 8 through 12 illustrate an alternate embodiment using a more simplified rotating aperture bar assembly generally referred to as 56'. In a fashion similar to the placement of bar assembly 56, bar assembly 56' is positioned within the scatter shield 48 in the orientation illustrated in FIG. 1. Aperture bar assembly 56' is an elongated cylindrical copper bar having a radial shaft 68 extending centrally therethrough. The shaft 78 is ideally of constant thickness and diverges at either end 69 in conformity with the width of the diverging fan beam. The bar may be of a sandwich composition as shown in FIG. 9 and be provided with diametrically opposed pair of steel stiffeners 70 attachable by means of screws 75 (see FIG. 11) to ensure the constant width of shaft 78 along the length of the bar. The sandwich composition may be conveniently secured together by fasteners 77 as shown in FIG. 10.

In this embodiment, the inner walls 71 and 72 of bar assembly 56' serve as the beam thickness defining members. Inner wall 71 is provided with a slightly chamfered portion 73 along one edge thereof while inner wall 72 has a similar chamfered portion 74 diametrically opposed to the chamfered portion 73. The orthogonal separation between the two chamfered portions 73 and 74 define the beam thickness in much the same fashion as the orthogonal separation between tips 60a of the mask pair 60 of the preferred embodiment. Thus, as shown in FIG. 12, a somewhat angled orientation of the rotatable bar assembly 56' relative to the North and South position creates a relatively thin slice while a slight counterclockwise rotation from that orientation as shown in FIG. 11 results in a generally thick beam slice.

The entire rotating aperture bar assembly 56' is motor driven by a motor connected to drive shaft 66. Again, beam thickness selection may be discrete or variable as described in connection with the preferred embodiment.

Another alternate embodiment is illustrated in FIGS. 13 through 17 showing a parallel aperture assembly 56".

In this third embodiment, a pair of elongated T-shaped bar sections 100 are substituted for the cylindrical bar assemblies of the previous embodiments. The T-shaped members 100 are also housed in the scatter shield 48 and, although arranged for rotation, their inner faces 102 move parallel toward one another in the orthogonal direction and hence the separation between them defines the beam thickness. Hence, the T-shaped bar sections 100 function as beam thickness defining members. The T-shaped members 102 may include lead shields 107 to further provide shielding against scattered radiation.

As shown generally in FIG. 13, the two T-shaped members 100 may be rotatably moved relative to one another in the orthogonal direction by the pivot assembly generally referred to as 103. Shaft 104 of the pivot assembly is arranged for clockwise and counterclockwise rotation with the aid of bearings 109 and may conveniently be connected to a drive motor by link 106. As pivot assembly 103 is rotated the orthogonal spacing between interfaces 102 varies thereby varying the slice thickness of the fan shaped radiation beam. The selected slice thickness is more accurately retained by the aid of biasing spring 111.

Referring now to FIG. 18 of the drawings, there is disclosed by way of example circuitry provided for controlling any of the alternate aperture assemblies contained within scatter shield 48. The thickness selector switch 200 is controlled by the scanner operator to selectively cause the aperture assembly within the scatter shield to be rotated so that the thickness of the X-ray beam may be varied.

When it is desired to adjust the thickness of the X-ray beam utilized by the scanner, the thickness selector switch 200 is actuated to cause the aperture assembly to rotate such that the orthogonal spacing between a pair of beam thickness defining members is varied. When the thickness selector switch 200 is switched from a first to a second state, a signal corresponding to the second state is transmitted to a thickness selector 202. The thickness selector 202 may comprise an analog multiplexer that selects one of two reference voltages from a voltage source 204 and causes the selected reference voltage to be output to a position comparator 206. The position comparator 206 has a second input for receiving input from a potentiometer 208. The output of the potentiometer 208 is a voltage level which varies in accordance with the position of the movement of the rotatable aperture assembly 56, 56' or 56".

The position comparator 206 will compare the selected voltage from the thickness selector 202 to the voltage output provided by the potentiometer 208 and will generate an error signal when a difference exists between the potentiometer output voltage and the selected reference voltage. A positive output error signal will be provided by the position comparator 206 when the selected reference voltage is smaller than the potentiometer output voltage, and a negative error signal will be provided when the selected reference voltage is larger than a potentiometer output voltage. In an exemplary embodiment, the first reference voltage is +4.5 volts and the second reference voltage is +3.0 volts. The first and second reference voltages are associated with the first and second states, respectively. Since the gain of the position comparator 206 is typically a gain of 10, a large error voltage of plus or minus 12 volts will typically be provided at the output of the position comparator 206 when a change in the switch setting has been made.

The error signal is transmitted from the position comparator 206 to a bi-directional motor drive circuit 210 via amplifier 212 and to error comparator 214. Normally, an input to the motor drive 210 causes the motor 216 to rotate and thus causes the beam thickness defining members to vary their orthogonal displacement as described above. However, a motor drive clamp circuit 216 is provided which is used to selectively disable the motor drive 210.

The motor drive clamp circuit 216 is controlled by the output from error comparator 214. The error comparator 214 is responsive to both positive and negative error signals. The output of the error comparator 214 will toggle between plus and minus 12 volts depending on the level of its input signals. When the thickness selector switch 200 is at a preset position, the output of the error comparator 214 is minus 12 volts because the motor drive clamp output feedback 218 maintains a minus 1 volt signal at the non-inverting input of the error comparator 214, and the error signal provided by position comparator 206 is near zero volts. The error signal from comparator 206 must therefore exceed a magnitude plus or minus 1 volt in order to toggle the error comparator 214. This condition occurs only when a new reference voltage corresponding to a new beam is selected by the thickness selector switch 200.

When a new beam thickness is selected, an error signal of approximately 12 volts will be output by the position comparator 206 to cause the error comparator 214 output to switch to plus 12 volts which will drive the motor drive clamp 216 output to minus 12 volts. The minus 12 volt output of the motor drive clamp 216 produces two results. First, motor clamping is removed from the motor drive; and second, the minus one volt from the motor drive clamp 216 is changed to 0.1 V to the error comparator 214 input. This condition allows the rotating aperture to gradually approach the desired position where motor clamping is reapplied.

With motor clamping removed, the motor drive circuitry is free to respond to error signals generated by the position comparator 206. The motor drive circuitry includes an error amplifier 212 and a bi-directional motor drive which applies positive or negative voltages to the motor 217.

As the rotatable aperture is driven into the proper position by the motor 217, the error signal voltage from the position comparator 206 will gradually reduce. When the error signal voltage falls below 800 millivolts, the motor drive circuitry will begin to reduce motor speed to prevent overshooting the desired position. The error signal will continue to decrease until about 100 millivolts. The error comparator 214 will then remove the plus 12 volts to the motor drive clamp 216 which will cause the output of the motor drive clamp 216 to inhibit the motor drive 210 and also change signal 218 from 0.1 V back to 1.0 V thus increasing the magnitude of the error necessary to turn the circuit back on to ±1.0 V. With the movable aperture thus locked in position by the motor clamp circuitry 216, a new image thickness selection is required before the motor 217 will again move.

We claim:

1. In a tomographic apparatus for subjecting a planar slice of a body to a fan shaped beam of penetrating radiation and producing an image representative of the variation of attenuation of the beam in the planar slice, the apparatus having means for defining a scan circle, an arc of radiation detector means disposed at least partially around the scan circle and in substantial axial alignment with said beam of radiation, a source of diverging radiation positioned such that radiation from said source is emitted, passes through said scan circle, and is transmitted to the detector means, means for collimating the radiation emitted by said source to form a fan shaped incident beam having a fan angle corresponding to said scan circle and a thickness in a direction orthogonal to the plane of said scan circle the improvement comprising:
   (a) an X-ray opaque rotatable elongated bar having a longitudinal axis about which said bar rotates and a radial slot extending through said bar transverse to said axis and defining a pair of uniformally spaced apart parallel interior walls in said bar defining planes equidistant from said longitudinal axis; and
   (b) means for rotating said bar such that the orthogonal spacing between said walls varies, said orthogonal spacing defining the thickness of the attenuated fan beam that is transmitted therethrough for limiting the amount of radiation received by said radiation detector means.

2. In a tomographic apparatus for subjecting a planar slice of a body to a fan shaped beam of penetrating radiation and producing an image representative of the variation of attenuation of the beam in the planar slice, the apparatus having means for defining a scan circle, an arc of radiation detector means disposed at least partially around the scan circle and in substantial axial alignment with said beam of radiation, a source of diverging radiation positioned such that radiation from said source is emitted, passes through said scan circle, and is transmitted to the detector means, means for collimating the radiation emitted by said source to form a fan shaped incident beam having a fan angle corresponding to said scan circle and a thickness in a direction orthogonal to the plane of said scan circle, the improvement comprising:
   (a) an X-ray opaque rotatable elongated bar having a longitudinal axis and a radial slot of predetermined thickness extending through a preselected length of said bar, wherein the thickness of said slot is generally uniform throughout said length relative to said bar and defining a variable orthogonal spacing within said bar relative to the plane of said scan circle, said bar positioned between said scan circle and at least a portion of said arc of detector means on the side of said scan circle opposite said source for the passage therethrough of the transmitted beam of radiation after its passage through the scan circle; and
   (b) means for rotating said bar to vary the orthogonal spacing therebetween, said orthogonal spacing defining the thickness of the attenuated transmitted fan beam for limiting the amount of radiation received by said radiation detector means.

3. In a tomographic apparatus according to claim 1 further comprising a scatter shield disposed between said scan circle and the radiation detector means, said scatter shield having a diverging inlet opening for defining the cross sectional dimensions of the transmitted beam and wherein the slot in said bar is also divergent through said bar.

4. In a tomographic apparatus according to claim 3 wherein said bar is rotatably attached within said scatter shield.

5. In a tomographic apparatus according to claim 2 wherein said elongated bar rotates about its longitudinal axis and wherein said axis is centrally located relative to the thickness of the attenuated transmitted fan beam.

6. In a tomographic apparatus according to claim 2 further comprising means attached to said bar for maintaining said slot at a constant thickness as said bar rotates.

7. In a tomographic apparatus according to claim 6 wherein said means for maintaining the slot at a constant thickness comprises at least one pair of diametrically opposed stiffeners attached to said bar.

* * * * *